(12) United States Patent
De Smet et al.

(10) Patent No.: US 10,976,638 B2
(45) Date of Patent: Apr. 13, 2021

(54) THERMOPLASTIC OPTICAL DEVICE

(71) Applicant: SIHTO NV, Zwijnaarde (BE)

(72) Inventors: Jelle De Smet, Aalst (BE); Paul Marchal, San Francisco, CA (US); Xiaobing Shang, Ghent (BE)

(73) Assignee: SIHTO NV, Zwijnaarde (BE)

( * ) Notice: Subject to any disclaimer, the term of this patent is extended or adjusted under 35 U.S.C. 154(b) by 0 days.

(21) Appl. No.: 15/618,070

(22) Filed: Jun. 8, 2017

(65) Prior Publication Data

US 2017/0357141 A1  Dec. 14, 2017

(30) Foreign Application Priority Data

Jun. 10, 2016 (EP) ..................... 16173913

(51) Int. Cl.
| | | |
|---|---|---|
| *G02B 27/42* | (2006.01) | |
| *G02F 1/29* | (2006.01) | |
| *B29D 11/00* | (2006.01) | |
| *A61F 2/16* | (2006.01) | |
| *G02C 7/08* | (2006.01) | |

(52) U.S. Cl.
CPC .............. *G02F 1/29* (2013.01); *A61F 2/1627* (2013.01); *B29D 11/00817* (2013.01); *G02B 27/4205* (2013.01); *G02C 7/083* (2013.01); *G02C 2202/20* (2013.01); *G02F 2001/294* (2013.01); *G02F 2201/305* (2013.01)

(58) Field of Classification Search
CPC ................. G02F 1/29; G02F 2001/294; G02F 2001/305; A61F 2/1627; B29D 11/00817; G02B 27/4205; G02C 7/083; G02C 2202/20

USPC ..... 349/13, 153, 155, 158, 187; 351/159.03, 351/159.39, 159.4, 159.38
See application file for complete search history.

(56) References Cited

U.S. PATENT DOCUMENTS

| | | | |
|---|---|---|---|
| 5,805,336 A * | 9/1998 | Dalzell | ............. B29D 11/0073 264/1.32 |
| 7,341,441 B2 * | 3/2008 | Ogino | .................. B29C 59/002 425/385 |
| 7,728,949 B2 | 6/2010 | Clarke et al. | |

(Continued)

FOREIGN PATENT DOCUMENTS

| | | |
|---|---|---|
| CN | 1599881 A | 3/2005 |
| CN | 101395520 A | 3/2009 |
| EP | 1 428 063 B1 | 6/2010 |
| EP | 2 562 593 A1 | 2/2013 |

OTHER PUBLICATIONS

European Search Report, European Patent Application No. 16173913.1, dated Nov. 16, 2016, 11 pages.

(Continued)

*Primary Examiner* — Travis S Fissel
(74) *Attorney, Agent, or Firm* — McDonnell Boehnen Hulbert & Berghoff LLP (57) ABSTRACT

The present disclosure describes optical devices and methods for manufacturing such optical devices. Namely, an example optical device includes a first optical transparent thermoplastic layer, a second optical transparent thermoplastic layer, and in between both thermoplastic layers, a diffractive optical element adjacent to one thermoplastic layer, a spacer in between the diffractive optical element and the other thermoplastic layer and, a border enclosing the diffractive element thereby forming a sealed cavity.

19 Claims, 7 Drawing Sheets

(56) References Cited

U.S. PATENT DOCUMENTS

| | | | |
|---|---|---|---|
| 2005/0073739 A1 | 4/2005 | Meredith et al. | |
| 2007/0040976 A1* | 2/2007 | Lee | G02F 1/133707 |
| | | | 349/134 |
| 2007/0159562 A1* | 7/2007 | Haddock | G02C 7/083 |
| | | | 349/13 |
| 2007/0195421 A1* | 8/2007 | Lin | B29D 11/0074 |
| | | | 359/619 |
| 2012/0212696 A1 | 8/2012 | Trajkovska et al. | |
| 2013/0107186 A1* | 5/2013 | Ando | G02C 7/083 |
| | | | 349/153 |
| 2013/0208238 A1 | 8/2013 | Blum et al. | |
| 2014/0211146 A1 | 7/2014 | Gupta et al. | |
| 2014/0347581 A1* | 11/2014 | Haddock | B29D 11/00028 |
| | | | 349/13 |

OTHER PUBLICATIONS

Liu, Yan Jun et al., "Nanoimprinted Ultrafine Line and Space Nanogratings for Liquid Crystal Alignment", Nanotechnology, vol. 23, No. 46, Oct. 23, 2012, pp. 1-6.
Li, Mingtao et al., "Fabrication of Circular Optical Structures with a 20 nm Minimum Feature Size Using Nanoimprint Lithography", Applied Physics Letters, vol. 76, No. 6, Feb. 7, 2000, pp. 673-675.
Kooy, Nazrin et al., "A Review of Roll-to-Roll Nanoimprint Lithography", Nanoscale Research Letters, vol. 9, Jun. 25, 2014, pp. 1-13.
Lin, Rongsheng et al., "Molecular-Scale Soft Imprint Lithography for Alignment Layers in Liquid Crystal Devices", Nano Letters, vol. 7, No. 6, 2007, pp. 1613-1621.
Chinese Office Action for Application No. 201780044157.6 dated Jan. 10, 2020.

* cited by examiner

THERMOPLASTIC OPTICAL DEVICE

CROSS REFERENCE TO RELATED APPLICATIONS

This application claims priority to European Patent Application No. 16173913.1, filed on Jun. 10, 2016, the contents of which are hereby incorporated by reference.

FIELD OF THE DISCLOSURE

The present disclosure relates to curved optical devices, in particular to curved optical devices comprising a liquid.

BACKGROUND

Presbyopia is a well-known disorder in which the eye loses its ability to focus at close distance, affecting more than 2 billion patients worldwide. Classic solutions include passive lenses such as reading glasses, progressive lenses or multifocal contact lenses. However, these passive lenses typically suffer from limited field-of-view, reduced contrast or long adaptation times.

Therefore, refocusable lenses, where the focal length of, a part of, the lens can be changed have attracted much attention in this field, as they would eliminate many of the known problems. Although some opto-mechanical solutions exist, electro-optical solutions are preferred as they are easier to reconfigure, have a faster response time and are mechanically more robust. Most electro-optical solutions require a cavity filled with one or more liquids and are generally using a liquid crystal based implementation. While Liquid Crystal Display technology is very mature, finding a way to integrate a refocusable liquid crystal lens in ophthalmic lenses has proven to be difficult, mainly because of the meniscus shape ophthalmic lenses generally have.

For instance, existing refocusable liquid crystal lenses are described in U.S. Pat. No. 7,728,949. This patent discloses lenses consisting of two plastic lens halves: a first curved lens half with a diffractive/refractive optical structure and a second lens half. On both lens halves transparent electrodes are deposited. The lens halves are glued together across the entire surface, except for the area of the optical structure; with a UV curable adhesive at the location of the optical structure a liquid crystalline material fills the gap between both lens halves. In the off-state the liquid crystal has the same index of refraction as the plastic substrate of the lens halves. It then conceals the diffractive/refractive structure and there is no lens action. By applying an electrical field between the lens halves, the index of refraction of the liquid crystalline material is modulated and it becomes different from the underlying diffractive/refractive optical structure, thereby leading to lens action.

The above approach, where the liquid crystal lens is directly made on two relatively thick (>1 mm) lens halves has a series of disadvantages. It is very difficult to manufacture in large volume because a conformal deposition of the electrode layer onto the curved surface of the diffractive/refractive optical structure is difficult to realize and may lead to yield and reliability issues. Obtaining a cost-effective and esthetically clean seal using a state-of-the art one-drop fill process is difficult to realize in ultra-thin lenses hence impeding high volume production of this approach. The diffractive/refractive optical structure can have a flat surface, but this limits the maximum diameter in typical thin lens designs where the flat lens needs to be somehow integrated between the curved back and front surfaces. The diffractive/refractive optical structure can be curved, but then the liquid crystal may spill over during the process, leading to contamination of the surfaces and bad adhesion of the glue. Filling the cavity post adhesion is another option but may leave the channel, through which the lens is filled, visible and compromises the aesthetics of the lens. One has to manufacture each lens blank separately, limiting the throughput. Since a polarization independent focal length change is generally required, one either needs to use a multi-layered lens structure with nematic liquid crystals, e.g. two layers with orthogonal alignment for both polarizations, or use a single layer combined with a cholesteric liquid crystal. The approach makes it really hard to create a multi-layer lens structure, forcing the use cholesteric liquid crystal to build a polarization independent lens with only one layer. However, it is known for people skilled in the state of the art that it is very difficult to control the haziness of the cholesteric layers, particularly thick layers, due to disclination lines and the large internal energy of the cholesteric layers. To avoid haziness of the cholesteric liquid crystals, one has to reduce the thickness of the liquid crystal layer, but this limits the blaze height forcing the use of a shorter pitch of the blazes in the optical diffractive/refractive structure, thereby increasing chromatic aberrations. As said, multi-layer lenses using nematic liquid crystals may result in a polarization independent lens with less haze, but the proposed approach will lead to lenses with a large thickness and many handling issues.

Another approach to address the above challenges may be to form a thin film liquid crystal layer first on a flat surface and then embed this flat surface it into passive lenses. An attempt hereto is disclosed in EP 1,428,063B1, describing a method for building electro-chromic lens inserts based on liquid crystal. The approach described is to manufacture first a liquid crystal device on a flat substrate. The device consists of two opposite facing substrates, on which transparent conductors are deposited, spaced from another using classical ball spacers or spherical polymer particles. The spacing is filled with a liquid crystal layer and sealed thereafter. The flat device is then thermoformed for integration in lens blanks. The described device does not have any lens action, i.e. it can be used to change the transparency of the lens, not the optical power.

Hence there is a need for a curved optical device with electrically tunable phase profile, e.g. a focal length change, whereby this device can be mass manufactured in a reliable way.

SUMMARY

In a first aspect an optical device is disclosed comprising a first optical transparent thermoplastic layer, a second optical transparent thermoplastic layer, and in between both thermoplastic layers, a diffractive optical element adjacent to the first thermoplastic layer, a spacer in between the diffractive optical element and the second thermoplastic layer and, a border enclosing the diffractive optical element thereby forming a sealed cavity. The optical device thus contains a sealed cavity formed by a first thermoplastic layer and a second thermoplastic layer and a border in between both thermoplastic layers. In area enclosed by the border a diffractive optical element and a spacer are present. The border can comprise, remote from the cavity, a notch containing an adhesive in contact with the second thermoplastic layer. The cavity of such an optical device is filled with a liquid crystalline material. In some embodiments, a channel is present extending through the border into the cavity, which channel allows filling the cavity with the liquid crystalline material.

In one embodiment, the spacer and the diffractive optical element can be stacked on each other, such that this stack maintains a controlled distance between both thermoplastic layers. To improve the alignment of a liquid crystalline material when present, the surface of the diffractive optical element, facing the second thermoplastic layer, contains submicron grooves configured as an alignment layer for a liquid crystalline material. Additionally, a conformal alignment layer can be present covering at least part of the grooves.

In another embodiment, a layer of a planarizing material can be present, covering the diffractive optical element and whereby at least part of the border adjacent to the diffractive optical element is made of the planarizing material. Now the spacer, the planarizing layer and the diffractive optical element are stacked on each other, whereby this stack maintains a controlled distance between both thermoplastic layers. To improve the alignment of a liquid crystalline material when present, the surface of that part of the planarizing layer covering the diffractive optical element, facing the second thermoplastic layer, contains submicron grooves configured as an alignment layer for a liquid crystalline material. Additionally, a conformal alignment layer can be present covering at least part of the grooves. The border can comprise, remote from the cavity, a notch now formed in the planarizing material, whereby the notch contains an adhesive in contact with the second thermoplastic layer.

In an example embodiment, the diffractive optical element, the spacer and the border are of the same material composition, allowing formation of these components by nanoimprint in the same layer stack.

The optical device can further comprise a first optical transparent electrode adjacent to the first optical transparent thermoplastic layer, a second optical transparent electrode adjacent to the second optical transparent thermoplastic layer, whereby at least the cavity is in between both optical transparent electrodes such that, when in use, an electrical field is applied at least over the liquid crystalline material when present in the cavity. The first transparent electrode can be positioned in-between the diffractive optical element and the first optical transparent thermoplastic layer, whereby the diffractive optical element and the cavity are in between both electrodes. Alternatively, the first transparent electrode is on the surface of the diffractive optical element facing the other optical transparent thermoplastic layer.

Furthermore, the optical device can be curved, i.e. both optical transparent thermoplastic layers have a predetermined curvature.

In a second aspect an optical instrument is disclosed comprising at least an optical device according to the first aspect. The optical device is configured to, when in use, tune the phase profile of the light towards the eye. An example of such an optical instrument is a lens. The optical instrument can contain more than on optical device according to the first aspect, e.g. a stack of two of such optical devices.

In a third aspect a method is disclosed for manufacturing an optical device according to the first aspect. Such a method of manufacturing this optical device, comprises providing a first optical transparent thermoplastic layer, forming by nanoimprint on the first optical transparent thermoplastic layer, at least one of a spacer, an optical diffractive element and a border enclosing the optical diffractive element and the spacer, and, providing a second optical transparent thermoplastic layer thereby forming a sealed cavity containing the spacer and the optical diffractive element whereby the spacer is in between the optical diffractive element and the second optical transparent thermoplastic layer. When nanoimprinting the spacer, the optical diffractive element and the border enclosing the optical diffractive element, a notch can be formed forming in the border, remote from the cavity. This notch is configured to contain an adhesive in contact with the second thermoplastic layer, which adhesive is provided in the notch only before the second optical transparent thermoplastic layer, is applied.

A liquid crystalline material can be provided over the optical diffractive element, the amount thereof is selected to fill only the sealed cavity when the second optical transparent thermoplastic layer is provided. This liquid crystalline material can be provided to the cavity before the second optical transparent thermoplastic layer closes the cavity. Alternatively this liquid crystalline material can be provided to the closed cavity via a channel, formed at least in the upper part of the border, extending through the border into the cavity. This channel may be formed when nanoimprinting the border.

In one embodiment, the spacer, the optical diffractive element and the border enclosing the optical diffractive element are formed of the same material stack. Thereto a layer of a material composition is formed on the first optical transparent layer, and, in this layer the spacer, the optical diffractive element and the border enclosing the optical diffractive element are nanoimprinted, whereby the spacer and the optical diffractive element are stacked on each other thereby maintaining a controlled distance between both thermoplastic layers. During this nanoimprint step submicron grooves can be formed in the surface of the optical diffractive element facing the second thermoplastic layer, the submicron grooves being configured as an alignment layer for a liquid crystalline material. Optionally a conformal alignment layer (not shown) can be deposited covering at least part of the grooves.

In another embodiment, a layer of planarizing material is provided thereby covering the diffractive optical element and at least part of the border adjacent to the diffractive optical element. In this planarizing layer the spacer and part of the border are nanoimprinted, whereby the spacer, the planarizing layer and the diffractive element are stacked on each other thereby maintaining a controlled distance between both thermoplastic layers. During this nanoimprint, submicron grooves can be formed in the surface of the planarizing layer facing the second thermoplastic layer, the submicron grooves being configured as an alignment layer for a liquid crystalline material. Additionally, a conformal alignment layer can be formed covering at least part of the grooves. If the planarizing material extends over the border, the notch can be nanoimprinted in this planarizing material.

The method can further comprise forming a first optical transparent electrode adjacent to the first optical transparent thermoplastic layer, forming a second optical transparent electrode adjacent to the second optical transparent thermoplastic layer, whereby at least the cavity is in between both optical transparent electrodes.

This method can include forming by nanoimprint an array of: a spacer and an optical diffractive element, both enclosed by a border.

If an array of optical devices is formed, this array is singulated into individual optical devices. The optical device can then be thermoformed thereby given each optical transparent thermoplastic layer a predetermined curvature.

A stack of two such optical devices can be formed applying the methods discussed in this third aspect. Either by manufacturing an array of optical devices and stacking two singulated optical devices. This stack of two optical devices may be thermoformed, thereby given each optical transparent thermoplastic layer a predetermined curvature. Alternatively, the process sequence discussed in this third aspect can be repeated as many times as the number of optical devices to be included in the stack. The method of manufacturing then comprises manufacturing a first optical device according to the first aspect by applying a method as disclosed in this third aspect, then manufacturing on the first optical device a second optical device according to the first aspect, whereby the second optical transparent thermoplastic layer of the first optical device serves as the first optical transparent thermoplastic layer of the second optical device. If an array is formed, this array is singulated to yield the stack of two optical devices. This stack of two optical devices can then be thermoformed thereby given each optical transparent thermoplastic layer a predetermined curvature.

BRIEF DESCRIPTION OF THE FIGURES

The above, as well as additional, features will be better understood through the following illustrative and non-limiting detailed description of example embodiments, with reference to the appended drawings.

For a better understanding of the present disclosure, some exemplary embodiments are described below in conjunction with the appended figures and figures description, wherein:

FIGS. 7(*a*) to (*d*) illustrate example embodiments of a method of manufacturing an optical device.

FIGS. 8(*a*) to (*e*) illustrate an example embodiment of a method of manufacturing an optical device.

FIGS. 9(*a*) to (*b*) illustrate an example embodiment of a method of manufacturing an optical device: (a) side view, (b) horizontal cross section A-A.

TABLE 1 feature - reference number overview

| Feature | Reference number | Feature | Reference number |
|---|---|---|---|
| 1, 1' | Optical device | 2, 2' | First optical transparent thermoplastic layer |
| 3, 3' | Second optical transparent thermoplastic layer | 4, 4' | Diffractive optical element |
| 5, 5' | Spacer | 6, 6' | Border |

TABLE 1-continued feature - reference number overview

| Feature | Reference number | Feature | Reference number |
|---|---|---|---|
| 7, 7' | Cavity | 8, 8' | First optical transparent electrode |
| 9, 9' | Second optical transparent electrode | 10 | Liquid crystalline material |
| 11 | Alignment layer | 12 | Material composition (of 4, 5, 6) |
| 13, 13' | Planarizing layer | 14 | Grooves |
| 15 | Adhesive | 16 | Notch |
| 17 | planarizing material (of layer 13, notch 16) | 18 | Layer of material 12 |
| 19 | channel through border (6) | | |

All the figures are schematic, not necessarily to scale, and generally only show parts which are necessary to elucidate example embodiments, wherein other parts may be omitted or merely suggested.

DETAILED DESCRIPTION

Example embodiments will now be described more fully hereinafter with reference to the accompanying drawings. That which is encompassed by the claims may, however, be embodied in many different forms and should not be construed as limited to the embodiments set forth herein; rather, these embodiments are provided by way of example. Furthermore, like numbers refer to the same or similar elements or components throughout.

The present disclosure will be described with respect to particular embodiments and with reference to certain drawings but the disclosure is not limited thereto. The drawings described are only schematic and are non-limiting. In the drawings, the size of some of the elements may be exaggerated and not drawn on scale for illustrative purposes. The dimensions and the relative dimensions do not necessarily correspond to actual reductions to practice of the disclosure.

Furthermore, the terms first, second, third and the like in the description and in the claims, are used for distinguishing between similar elements and not necessarily for describing a sequential or chronological order. The terms are interchangeable under appropriate circumstances and the embodiments of the disclosure can operate in other sequences than described or illustrated herein.

Moreover, the terms top, bottom, over, under and the like in the description and the claims are used for descriptive purposes and not necessarily for describing relative positions. The terms so used are interchangeable under appropriate circumstances and the embodiments of the disclosure described herein can operate in other orientations than described or illustrated herein.

The term "comprising", used in the claims, should not be interpreted as being restricted to the means listed thereafter; it does not exclude other elements or steps. It needs to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting of only components A and B. It means that with respect to the present disclosure, the only relevant components of the device are A and B.

In a first aspect an optical device (1) is disclosed comprising a first optical transparent thermoplastic layer (2), a second optical transparent thermoplastic layer (3), and in between both thermoplastic layers (2,3), a diffractive optical element (4) adjacent to the first thermoplastic layer (2), a spacer (5) in between the diffractive optical element (4) and the second thermoplastic layer (3) and, a border (6) enclosing the diffractive optical element (4) thereby forming a cavity (7). The optical device (1) thus contains a sealed cavity (7) formed by the first thermoplastic layer (2), the second thermoplastic layer (3) and the border (6) positioned in between both thermoplastic layers (2,3). Inside the cavity area encircled by the border, the diffractive optical element (4) and the spacer (5) are present.

A thermoplastic, or thermosoftening plastic, is a plastic material, a polymer, which becomes pliable or moldable above a specific temperature and solidifies upon cooling. In an example embodiment, these thermoplastic layers are made from polymers which are optically transparent: i.e. having between 5 and 100% light transmission efficiency in the visual spectrum e.g. 400-700 nm. Examples are polyethylene terephthalate, cellulose triacetate, transparent polyurethane polycarbonate, or thiourethane materials used for making eyeglasses such as Mitsui MR8. The films made of these materials may have thicknesses that vary between 5 and 1000 μm and typically withstand bending radii up to 3 mm.

The diffractive optical element may comprise a diffractive structure such as blazed gratings, Fresnel lenses, Fresnel axicons or other structures which induce a predetermined phase profile in the transmitted light.

Figure 1:
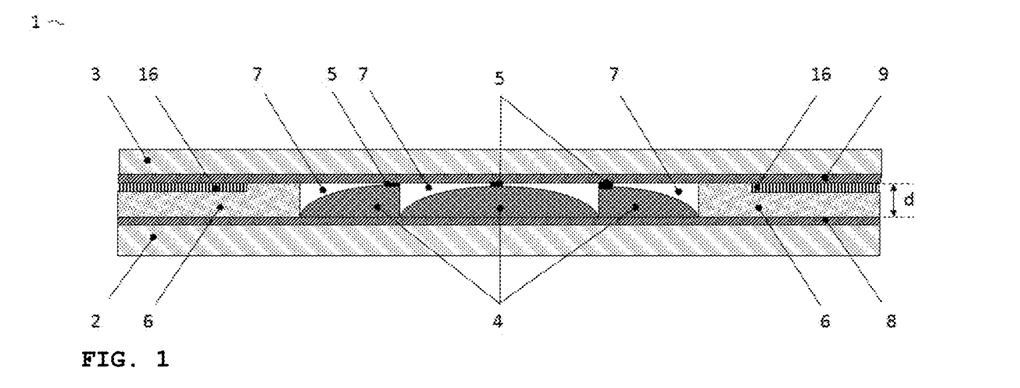
FIG. 1 illustrates an optical device prior to thermoforming according to an example embodiment.

An example of an implementation of such an optical device (1) is shown in FIG. 1. As disclosed in embodiments below, the device shown in FIG. 1 further contains a pair of optical transparent electrodes (8,9) at opposite sides of the cavity (7) positioned as to apply an electrical field over a liquid crystalline material (10) when present in the cavity (7). This device further comprises notches (16), formed in the border (6), containing an adhesive (15). The upper part of the device, with the second optical transparent thermoplastic layer (3) on which the second optical transparent electrode (9) is the formed, is hence attached to the border (6) by this adhesive (15).

In an example embodiment, a notch (16) is formed in the border (6). When a liquid crystalline material (10) fills the cavity (7) and an adhesive (15) fills the notch (16), both materials are spaced apart by the sidewall of the border (6) adjacent to the diffractive optical element (4) as illustrated by FIG. 1. This spacing prevents spill-over and/or cross-contamination when sealing the cavity (7) when providing the second optical transparent thermoplastic layer (3).

Figure 9:
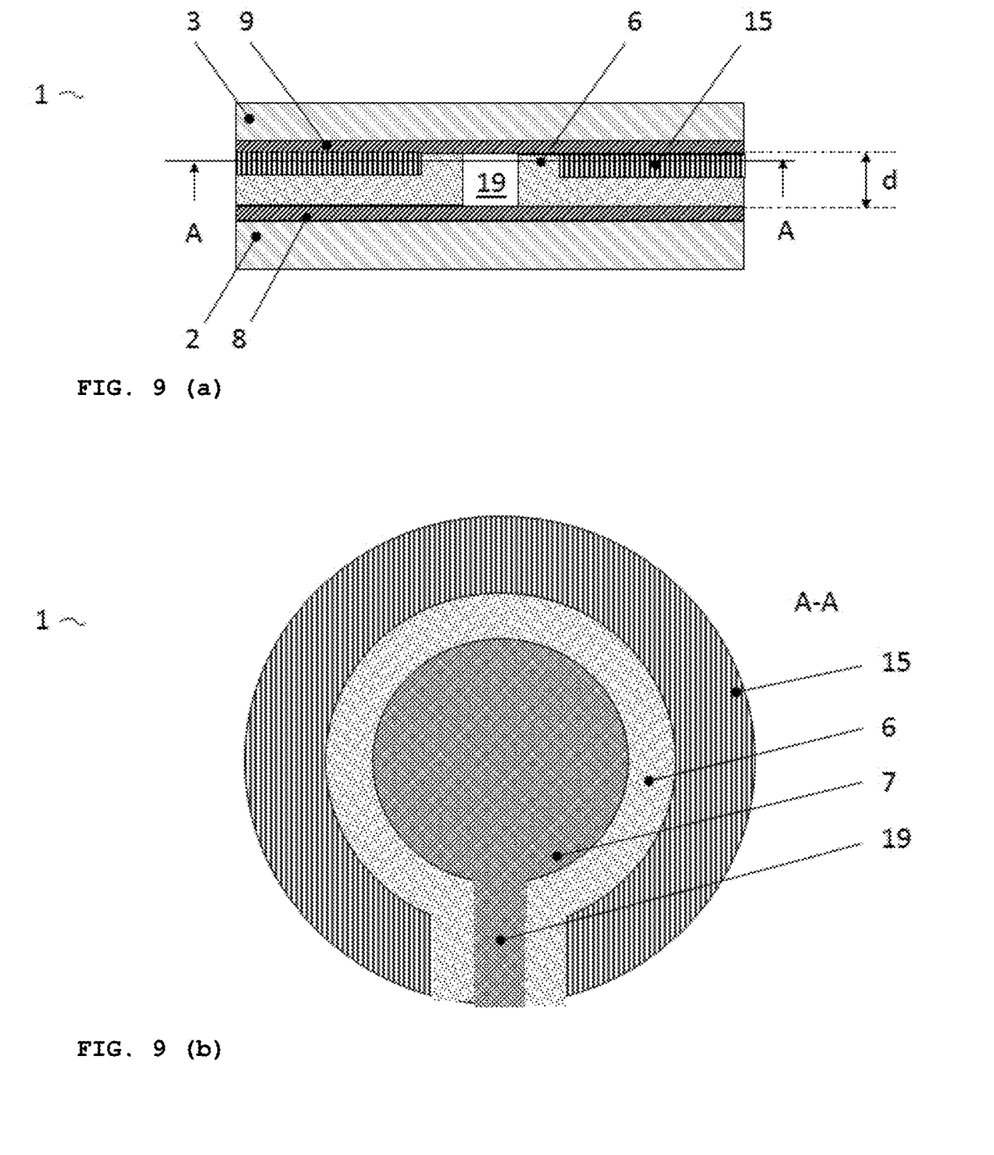

As discussed in the third aspect, a channel (19) can be present in the border (6), giving passage to the cavity (7) even after closure thereof by the second optical transparent thermoplastic layer (3). FIG. 9 shows a side view and a horizontal cross-section AA thereof of an optical device (1) containing such a channel (19). In one embodiment the channel (19) extends over the full width of the border (9).

The fluid material filling the cavity (7) can be a liquid crystalline material, a variable refractive index polymer material, variable dye, an electro chromic electrolyte, or a resin. In an example embodiment, the index of refraction of the liquid crystalline material (10) is matched with the index of refraction of the diffractive optical element (4), the border (6) and the adhesive (15) at least for one of the states of the liquid crystalline material (10). For instance, the ordinary index of refraction of the well-known liquid crystal E7 is equal to the UV glue NOA74.

In an example embodiment, the bottom substrate containing the first optical transparent thermoplastic layer (2), and when present the first optical transparent electrode (8), and the upper substrate containing the second optical transparent thermoplastic layer (3), and when present the second optical transparent electrode (9), are at a fixed distance (d) set by a stack of a spacer (5) on top of the diffractive optical element (4) and, in parallel, by the border (6), both structures (5-4, 6) being positioned in between both substrates as illustrated by FIG. 1. This height can be between 10 nanometer (nm) and 100 micrometer (μm), typically between 50 nm and 50 μm.

In an example embodiment, the border (6), the spacer (5) and the diffractive optical element (4) have the same material composition (12). For example, the spacer (5), the diffractive optical element (4) and the border (6) can be made from a high-refractive-index monomer such as bisphenol fluorine diacrylate or high refractive index UV-glues such as NOA 1625 or NOA 164.

As disclosed below, the border (6), the spacer (5) and the diffractive optical element (4) can be formed using nanonanoimprint technology from the same layer (18), having this material composition (12), present on the bottom substrate.

Figure 3:
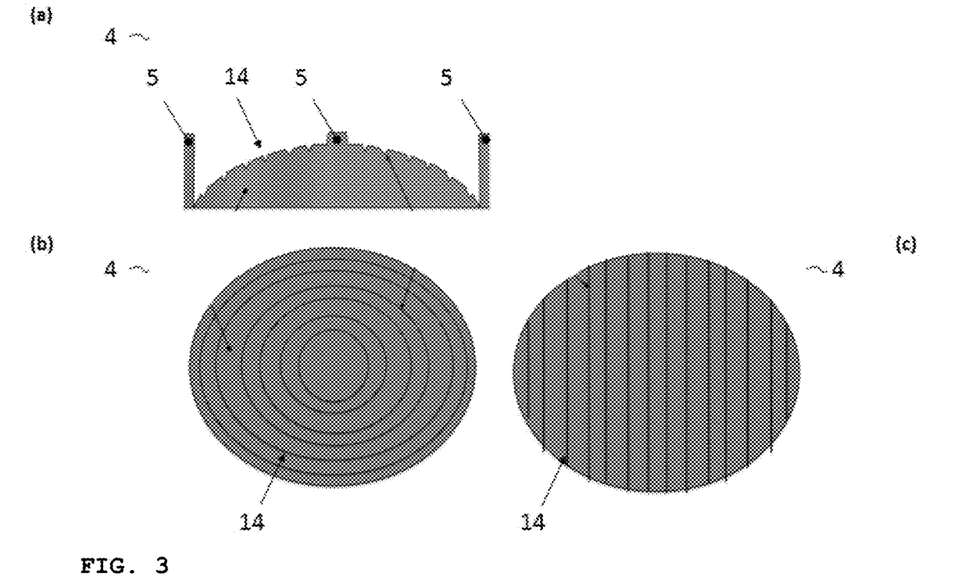
FIG. 3 illustrates a diffractive optical element with grooved surface according to an example embodiment: (a) cross-section, (b) top view of (a) with circular grooves, (c) top view of (a) with parallel grooves.

In an example embodiment, the surface of the diffractive optical element (4), which surface is oriented towards the second thermoplastic layer (3) contains submicron grooves (14) configured as an alignment layer (11) for a liquid crystalline material (10). During operation of the device (1) these grooves assist in orienting the liquid crystals present in the cavity (7). In an example embodiment, another alignment layer (11) is also present at the side of the cavity (7) adjacent to the second optical transparent electrode (3) thereby facing the grooved surface. FIG. 3(a) is a cross-sectional view showing how these grooves (14) are present in the three-dimensional surface of the diffractive optical element (4). FIG. 3(b) gives a top view of this surface when the grooves have a circular pattern, while FIG. 3(c) gives a top view of this surface when the grooves have a parallel pattern. In FIG. 3 one also notice that in this embodiment the spacer (5) on top of the diffractive optical element (4) and the diffractive optical element (4) are formed from the same material as discussed in the paragraphs above.

These grooves can be created when forming the diffractive optical element (4) by nanoimprint as discussed in the previous paragraphs. The mold used in the nanoimprint process contains not only the negative shape of the border (6), the spacer (5) and the diffractive optical element (4), but its inner surface, at least at the location of the shape of diffractive optical element (4), contains grooves in e.g. a circular or rectangular pattern. This approach allows forming these 4 features (4, 5, 6, 14) in an integral way. Y. J. Liu et al discloses forming such alignment patterns using nanoimprint technology in 'Nanoimprinted ultrafine line and space nano-gratings for liquid crystal alignment', as does R. Lin et al. in 'Molecular-Scale Soft Imprint Lithography for Alignment'.

The alignment properties of the liquid crystalline material (10) are not only determined by the geometry of grooves (14) themselves, but also by the material constituting the diffractive optical element (4) in which the grooves are formed. If another material is used for the same configuration of the grooves, an additional conformal alignment layer (not shown) can be formed overlying these grooves (14) to provide different material alignment properties. For instance, a homeotropic alignment layer might be coated, overlaying at least some of the grooves if the material of the diffractive optical element aligns the liquid crystal molecules in a planar way. This conformal alignment layer can cover the complete grooved surface of the diffractive optical element (4). Alternatively only part of this grooved surface can be covered with this additional conformal alignment layer allowing to exploit the difference in material alignment properties between the additional conformal alignment layer (not shown) and the diffractive optical element (4).

Figure 4:
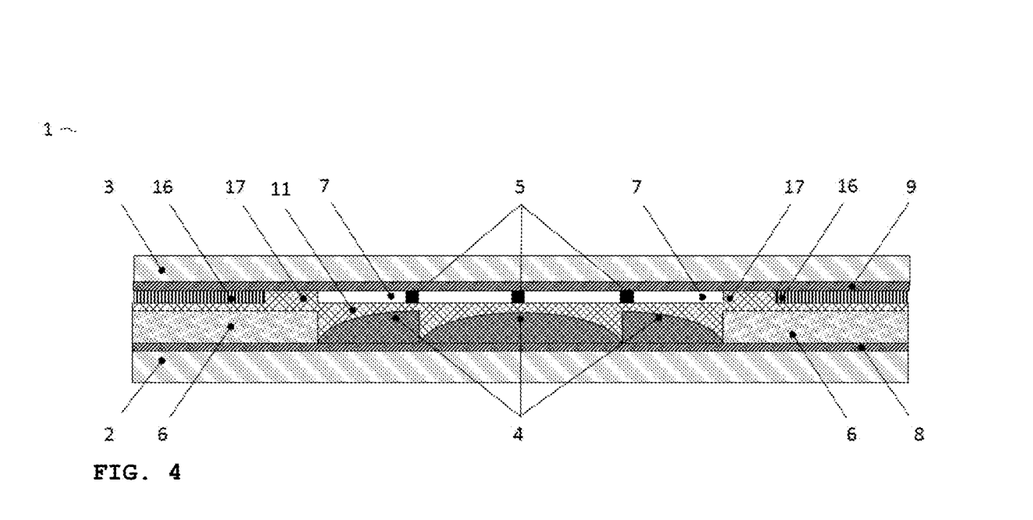
FIG. 4 illustrates an optical device with planarizing layer prior to thermoforming according to an example embodiment.

A layer (13) of a planarizing material (17) can be present inside the cavity (7) on top of the diffractive optical element (4) as illustrated by FIG. 4. Similar to the implementation illustrated by FIG. 3, an alignment layer (11) can be present at the bottom of the cavity (7), by grooves (14) formed in the surface of the planarizing layer (13), which surface is oriented towards the second thermoplastic layer (3). During operation of the device (1) these grooves assist in orienting the liquid crystals present in the cavity (7). In an example embodiment, another alignment layer (11) is also present at the side of the cavity (7) adjacent to the second optical transparent electrode (3), thereby facing the grooved surface.

The alignment properties of the liquid crystalline material (10) are not only determined by the geometry of grooves (14) themselves, but also by the material constituting the planarizing layer (13) in which the grooves are formed. If another material is used for the same configuration of the grooves, an additional conformal alignment layer (not shown) can be formed overlying these grooves (14) to provide different material alignment properties. For instance, a homeotropic alignment layer might be coated, overlaying at least some of the grooves if the material of the diffractive optical element aligns the liquid crystal molecules in a planar way. This conformal alignment layer can cover the complete grooved surface of the planarizing layer (13). Alternatively only part of this grooved surface can be covered with this additional conformal alignment layer allowing to exploit the difference in material alignment properties between the additional conformal alignment layer (not shown) and the planarizing layer (13)

The materials (12, 17) of respectively the diffractive optical element (4) and the planarization layer (13), at least at their interface, can have the same refractive index Furthermore, the dielectric constant at low frequency electric fields (e.g. 1 Hz-10 kHz) of the these materials (12, 17) may differ.

This planarizing material (17) can also be used to form the upper part of the border (6). If a notch (16) is present, it is formed in this planarizing material (17) as illustrated in FIG. 4. Compared to the optical device (1) illustrated by FIG. 1, in the optical device (1) of FIG. 4 the cavity (7) is bordered by this planarizing material (17) at its bottom and sides, and at its top by the upper substrate containing the second optical transparent thermoplastic layer (3), and when present the second optical transparent electrode (9).

In the implementation as illustrated by FIG. 4, the bottom substrate containing the first optical transparent thermoplastic layer (2), and when present the first optical transparent electrode (8), and the top substrate containing the second optical transparent thermoplastic layer (3), and when present the second optical transparent electrode (9), are at a fixed distance (d) set by the stack of a spacer (5) on top of the planarizing layer (13) covering the diffractive optical element (4) and, in parallel, by the border (6), both structures (4-5-13, 6) being positioned in between both substrates as illustrated by FIG. 4. This height can be between 10 nanometer (nm) and 100 micrometer (μm), typically between 50 nm and 50 μm.

As disclosed below, the spacer (5), and if present the notch (16), can be formed in the planarizing layer (13) overlying the bottom substrate using nanoimprint technology. When nanoimprinting the spacer (5) the cavity (7) is formed. Again, when a liquid crystalline material (10) fills the cavity (7) and an adhesive (15) fills the notch (16), both materials are spaced apart by the sidewall of the border (7) adjacent to the diffractive optical element (7) as illustrated by FIG. 4. This spacing prevents spill-over and/or cross-contamination when sealing the cavity (7) when providing the second optical transparent thermoplastic layer (3).

Figure 2:
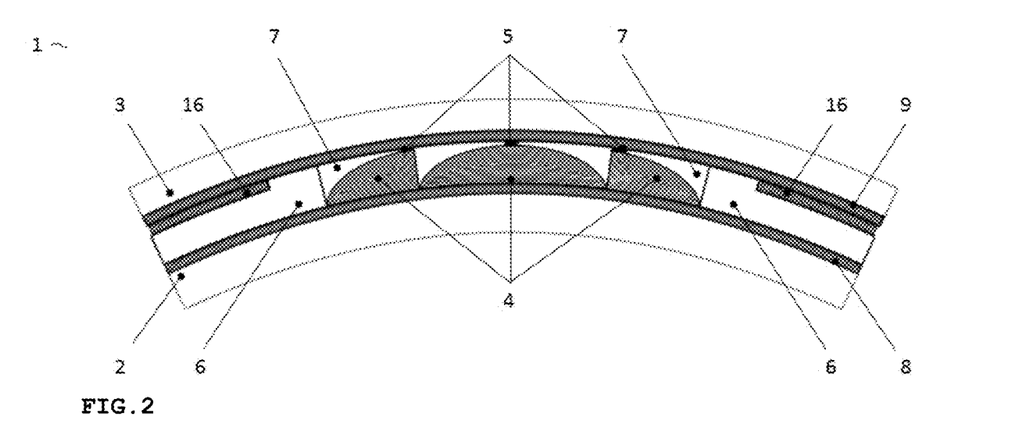
FIG. 2 illustrates the optical device of FIG. 1 after thermoforming according to an example embodiment.

An optical device (1) as illustrated in FIG. 1 or FIG. 3 is a planar device. If desired, a curved version of it can be obtained by subjecting the optical device (1) to a thermoforming process as will be discussed in the third aspect of this disclosure. In an example embodiment, the optical device (1) is spherically curved. A predetermined curvature of the thermoplastic layers (2,3) and hence of the optical device (1) can then be obtained as illustrated by FIG. 2. Such a curved optical device (1) can be used inter alia as lens insert, as will be discussed in the second aspect of this disclosure.

As already shown in FIG. 1, FIG. 2 and FIG. 4, the optical device (1) further can contain a pair of optical transparent electrodes (8,9) at opposite sides of the cavity (7). In an example embodiment, a first optical transparent electrode (8) is present adjacent to the first optical transparent thermoplastic layer (2), while a second optical transparent electrode (9) is present adjacent to the second optical transparent thermoplastic layer (3), whereby the diffractive optical element (4) is in between both optical transparent electrodes (8,9).

The second optical transparent electrode (9) is typically on the second optical transparent thermoplastic layer (3) at the side of the cavity (7) as illustrated by in FIG. 1, FIG. 2 and FIG. 4. The first optical transparent electrode (8) can be present in-between the diffractive optical element (4) and the first optical transparent thermoplastic layer (2) as illustrated in FIG. 1, FIG. 2 and FIG. 4. If a planarizing layer (13) is present, as illustrated by FIG. 4, this first optical transparent electrode (8) can be present in between this planarizing layer (13) and the diffractive optical element (4).

The electrode (8,9) configuration can allow a non-uniform electrical field to be applied over the liquid crystalline material (10) when present in the cavity (7). To this effect, the first optical transparent electrode (8) is located on top of the diffractive optical element (4) near the cavity. If the first optical transparent electrode (8) is located in-between the diffractive optical element (4) and the first optical transparent thermoplastic layer (2) as illustrated in FIG. 1, FIG. 2 and FIG. 4, a planarizing layer (17) is to be used having a dielectric constant that differs from the dielectric constant of the diffractive optical element (4).

The optical transparent electrodes can be made of materials such as Indium Tin Oxide (ITO), ClearOhm® silver nanowires or AGFA Orgacon inks. Because of the brittleness of ITO, less rigid and more flexible materials can be used such as PEDOT:PSS, graphene, carbon nanotubes or silver nanowires. The optical transparent electrodes (8, 9) can be patterned to individually address different zones of the diffractive optical element (4). These electrodes can also be patterned to reduce the overall capacity, e.g. by only having electrodes within the area of the diffractive optical element (4) or to separate the electrode within this area from electrode within the area of the border (6).

In a second aspect of this disclosure, optical devices (1) as disclosed in the previous aspect are used in optical instruments. When inserted in an optical instrument, the optical device (1) is configured to tune the phase profile of the light towards the eye.

Such an optical instrument can be a lens, where the optical device is used as a lens insert. When considering ophthalmic applications, the lens might be an eyeglass lens, a contact lens or an intraocular lens. Since both eyeglass lenses and contact lenses generally have a meniscus shape, the optical device can be more easily integrated in the lens, when the optical device (1) is also curved with a curvature substantially the same as the curvature of the lens in which it needs to be embedded. Typically, the optical device will then be curved in two orthogonal directions. For intraocular lenses, a planar or a curved optical device can be embedded.

Such optical instruments can contain more than one optical device (1). These optical devices (1,1') can be stacked. By stacking multiple optical devices (1,1'), the electro-optical properties of the single optical devices can be combined. For instance, two devices filled with nematic liquid crystal but with an orthogonal alignment can lead to a polarization independent tunable lens.

Figure 5:
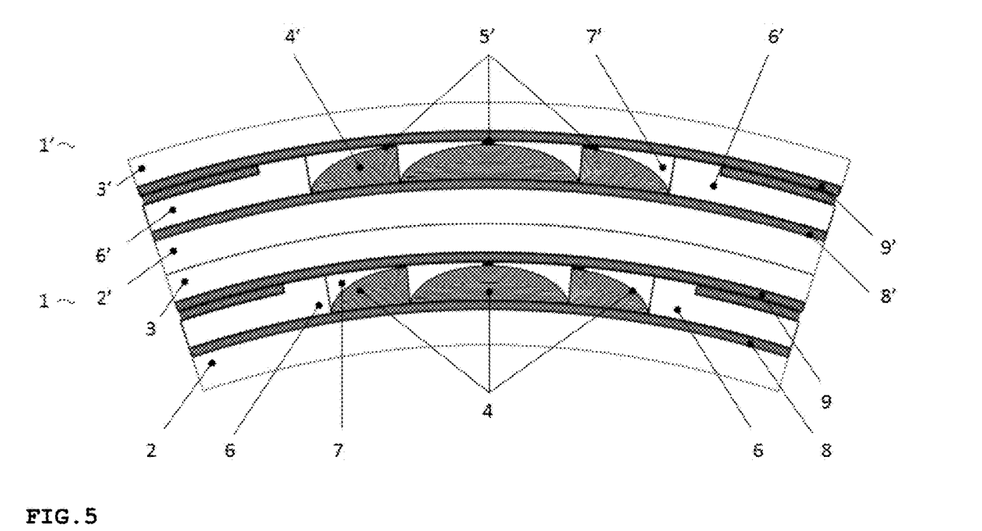
FIG. 5 illustrates an optical instrument containing a stack of optical devices of FIG. 2 according to an example embodiment.
Figure 6:
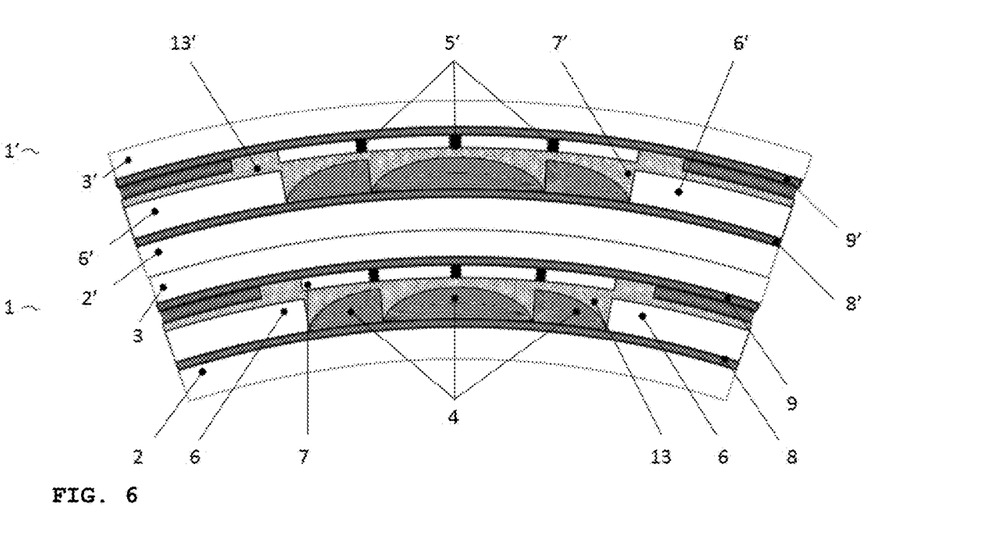
FIG. 6 illustrates an optical instrument containing a stack of optical devices of FIG. 4, when thermoformed, according to an example embodiment.

In the implementations illustrated by FIG. 5 and FIG. 6, optical devices (1,1') respectively without and with planarizing layer (13, 13') are stacked.

Figure 7A:
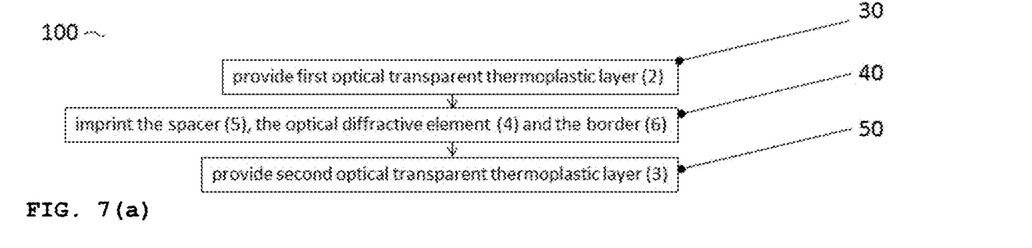

In a third aspect methods are disclosed for manufacturing optical devices according to the first aspect. Such methods (100) of manufacturing the optical device (1), comprises (30) providing a first optical transparent thermoplastic layer (2), (40) forming by nanoimprint on the first optical transparent thermoplastic layer (2), at least one of a spacer (5), an optical diffractive element (4) and a border (6) enclosing the optical diffractive element (4) and the spacer (5), and, (50) providing a second optical transparent thermoplastic layer (3) thereby forming a cavity (7) containing the spacer (5) and the optical diffractive element (4) whereby the spacer (5) is in between the optical diffractive element (4) and the second optical transparent thermoplastic layer (2). This method is illustrated by FIG. 7(a).

Nanoimprint technology is a simpler, lower-cost and high-throughput patterning technology compared to lithographic patterning used in semiconductor and flat panel manufacturing technology. As disclosed inter alia in 'A review of roll-to-roll nanoimprint lithography', by Kooy et al in Nanoscale Research Letters 2014, hereby incorporated by reference, nanoimprint lithography involves the use of a prefabricated mold containing an inverse of the desired pattern. This mold is pressed into a polymer-coated substrate whereby the pattern is replicated into the polymer by mechanical deformation thereof. After deformation the pattern is fixed using a thermal process on the deformed polymer or by exposing the deformed polymer to UV-light resulting in a hardening of the nanoimprinted pattern. Thereafter the mold is removed. The inverse pattern can correspond to a single structure to be formed. Forming an array of structures in the polymer then requires repeating the nanoimprint process as many times as the number of structures needed. The throughput can be increased if the mold contains an array of the inverse pattern, whereby during a single nanoimprint the desired number of structures is simultaneously formed in the same polymer.

Figure 7B:
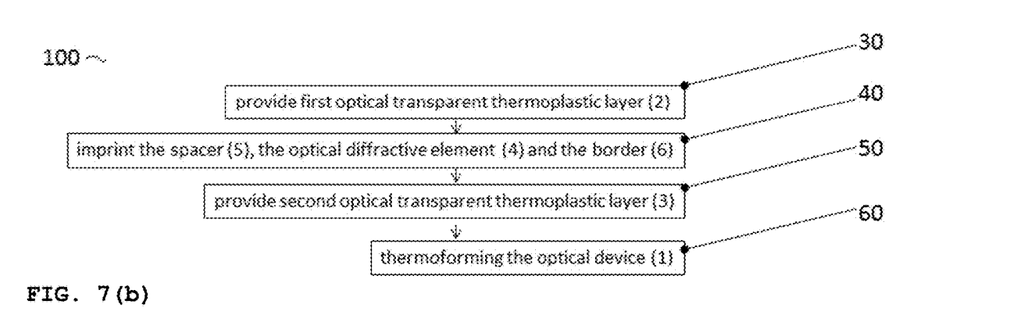
Figure 7C:
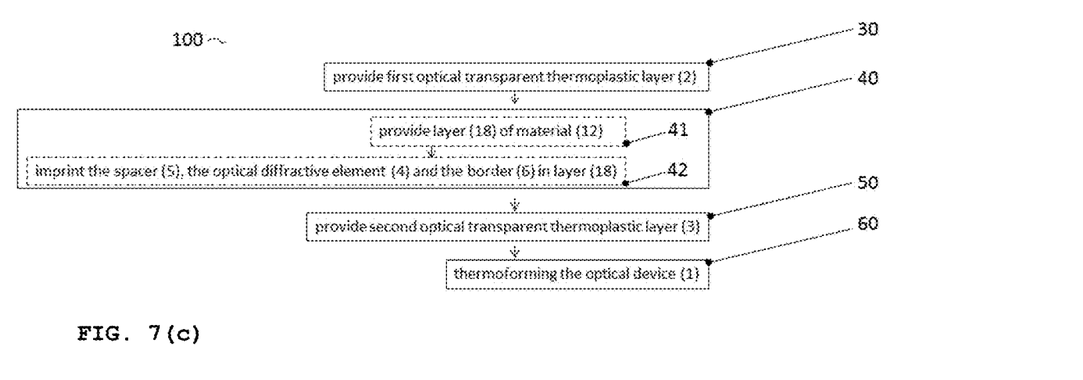
Figure 7D:
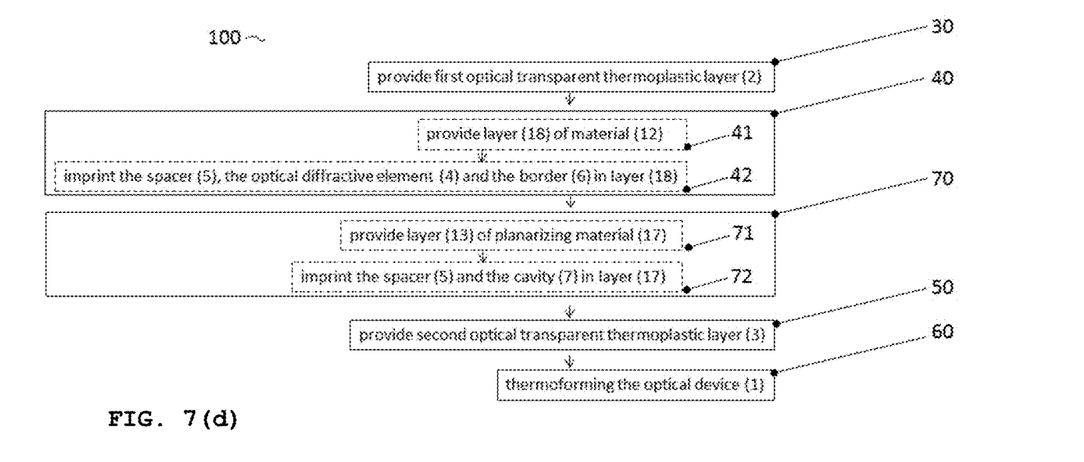

Implementations of this method (100) are further illustrated in FIG. 7(b) to (d). FIG. 7(b) illustrates the implementation whereby, the spacer (5), the optical diffractive element (4) and the border (6) enclosing the optical diffractive element (4) are formed by nanoimprint technology (40). As illustrated by FIG. 7(c), in such implementation a layer (18) of a material composition (12) can be provided (41) on the first optical transparent layer (2), or, if present on the first optical transparent electrode (8). In this layer (18) the spacer (5), the optical diffractive element (4) and the border (6) enclosing the optical diffractive element (4) are (42) nanoimprinted whereby all these elements have the same material composition. The spacer (5) and the optical diffractive element (4) are stacked on each other thereby maintaining a controlled distance (d) between both thermoplastic layers (2,3). FIG. 7(d) illustrates the implementation whereby after nanoimprinting the spacer (5), the optical diffractive element (4) and the border (6) a planarizing layer (13) is provided (71). In this planarizing layer (13) the spacer (5) and hence the cavity (7) is formed by another nanoimprint process (72).

As discussed in the first aspect, the bottom surface of the cavity (7), whether it is the surface of the diffractive optical element (4) or the surface the planarizing layer (13) covering this optical element (1), can be grooved during the respective nanoimprint process (32, 62) thereby forming an alignment layer (11) for a liquid crystalline material (10).

Likewise a notch (16) can be formed in the border (5), remote from the cavity (7). If a nanoimprint process is used to from the border (5), this notch (16) can also be formed during this nanoimprint process (32, 62).

The methods (100) discussed in the foregoing paragraphs can further comprise forming a first optical transparent electrode (8) adjacent to the first optical transparent thermoplastic layer (2), forming a second optical transparent electrode (9) adjacent to the second optical transparent thermoplastic layer (3), whereby at least the cavity (7) is in between both optical transparent electrodes (8).

The bottom substrate comprising on the first optical transparent thermoplastic layer (2), the spacer (5), the optical diffractive element (4) and the border (6), optionally the notch (16) in the border (6) is attached to top substrate comprising the second optical transparent thermoplastic layer (3), by providing, prior to providing the second optical transparent thermoplastic layer (3), an adhesive (15) in the notch (16) only.

Although in the methods discussed above, the manufacturing of a single optical device (1) was disclosed, multiple optical devices (1,1') can be manufactured using semiconductor or flat panel display manufacturing techniques. Instead of forming, e.g. by nanoimprinting in a layer (12), a single configuration of a spacer (5) and an optical diffractive element (4), enclosed by a border (6), one can form an array of such combinations, either in parallel or sequentially, resulting in an array of: a spacer (5) and an optical diffractive element (4), enclosed by a border (6). One or multiple devices can be extracted from the array by e.g. punching or laser cutting.

As illustrated by FIG. 7(b), after providing the second optical transparent thermoplastic layer (3), a planar optical device (1) is obtained as illustrated by FIG. 1 or FIG. 4. This planar optical device (1) can then be subjected to a thermoforming process resulting in a curved optical device (1) as illustrated by FIG. 2, whereby each optical transparent thermoplastic layer (2,3) has a predetermined curvature. During the thermoforming process, the optical device (1) is placed in a mold and heated until at least the glass transition temperature Tg of the optical transparent thermoplastic layers (2,3) is reached whereby the mechanical force applied let the thermoplastic layers assume the shape of the mold. The mold is then closed and cooled down below this glass transition temperature Tg to fix the shape of the deformed thermoplastic layers. Then the optical device (1), now curved, is released from the mold. Alternatively, the optical device can be clamped at its sides onto a single sided mold whilst heating. During the thermoforming process, the optical device can then be brought into the desired shape be creating a pressure difference over the optical device (1). Such a pressure difference can be obtained by creating a vacuum in between the optical device or the mold, or by creating a higher pressure atmosphere above the device than in between the device and the mold.

One can also stack optical devices (1, 1') on top of each-other. In one implementation two optical devices (1, 1') are manufactured, as discussed in the foregoing paragraphs of this third aspect. Both optical devices (1, 1') are stacked. This stack of optical devices (1,1') is then subjected to a thermoforming process resulting in a curved optical device (1) as illustrated by FIG. 5 or FIG. 6, whereby each optical transparent thermoplastic layer (2,3) has a predetermined curvature. In another implementation such stack of optical devices (1,1') is formed by manufacturing one optical device (1') on top of another optical device (1). In this implementation a first optical device (1) is manufactured as discussed in the foregoing paragraphs of this third aspect. On top of this optical device (1) a second optical device (1') is manufactured as discussed in the foregoing paragraphs of this third aspect. Instead of providing a first optical transparent thermoplastic layer (2') for this second optical device (1'), one can use the second optical transparent thermoplastic layer (3) of the first optical device (1) as the first optical transparent thermoplastic layer (2') of the second optical device (1'). Once the second optical device (1') is manufactured, it is stacked on the first optical device (1). Then the stack of two optical devices (1, 1') is thermoformed, thereby giving each optical transparent thermoplastic layer (2, 3, 2', 3') a predetermined curvature.

In FIG. 8(a) to (d), an implementation of this method is shown resulting in the optical device (1) illustrated by FIG. 1. In an example embodiment, the optical device is manufactured in a semiconductor or flat panel display fab allowing exploitation of the manufacturing process enabling mass scale production of the optical device (1) comparable to the manufacturing of semiconductor circuits or flat displays.

Figure 8A:
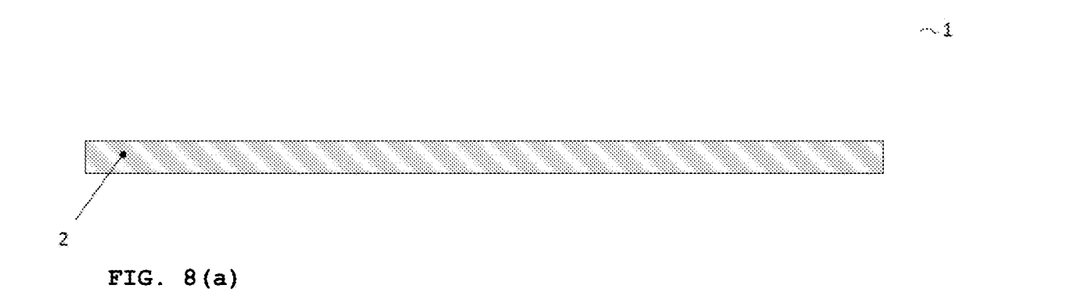

As a first step illustrated by FIG. 8(a), the first optical transparent thermoplastic layer (2) is formed on a temporary carrier (not shown). Most semiconductor or flat panel process equipment is configured to handle rigid panels or wafers having a diameter of 10 cm or more. Using such a temporary mechanical carrier, on which the different elements of the optical device (1) are formed, allows using this type of equipment which then results in a cost-efficient and reliable manufacturing process. It also ensures that the optical transparent thermoplastic layer or film (2) remains flat during processing of the optical device (1), thereby reducing the total thickness variation over the array of optical devices (1) manufactured. Reduced thickness variation is important for subsequent process steps, such as e.g., lithography and one drop fill process for providing the adhesive (15) and/or liquid crystalline material (10) when filling respectively the notch (16) and the cavity (7) without spill-over. Thanks to the size of the temporary mechanical carrier, multiple optical devices (1) can be manufactured on a single carrier enabling large throughput and hence lower cost per optical device (1).

The first optical transparent thermoplastic film (2) can be formed on the carrier by lamination. Typically the laminate film (2) is between 5 um and 1000 um thick. Alternatively, one may deposit a thermoplastic material in liquid form onto the carrier. The liquid material can then be either UV or thermally cured, thereby forming the first optical transparent thermoplastic film (2). Either way, a temporary adhesive may be needed to attach the first optical transparent thermoplastic film (2) to the carrier, allowing releasing the optical device (1) from the temporary carrier after completing of the processing. Temporary carrier solutions are available from companies such as TOK, Brewer Science, 3M, Nitto, etc. In some cases the film (2) is fixated by applying a vacuum in between the film and the carrier.

Figure 8B:
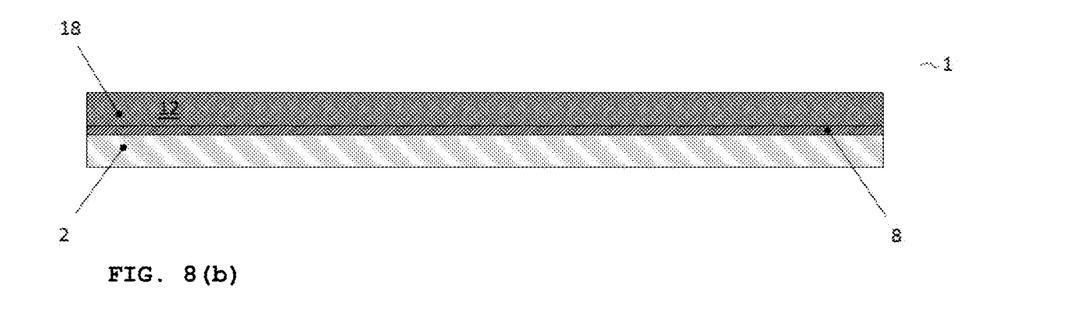

On the first optical transparent thermoplastic layer (2), a transparent conductive film is formed to manufacture the first optical transparent electrode (8) as shown in FIG. 8(b).

Figure 8C:
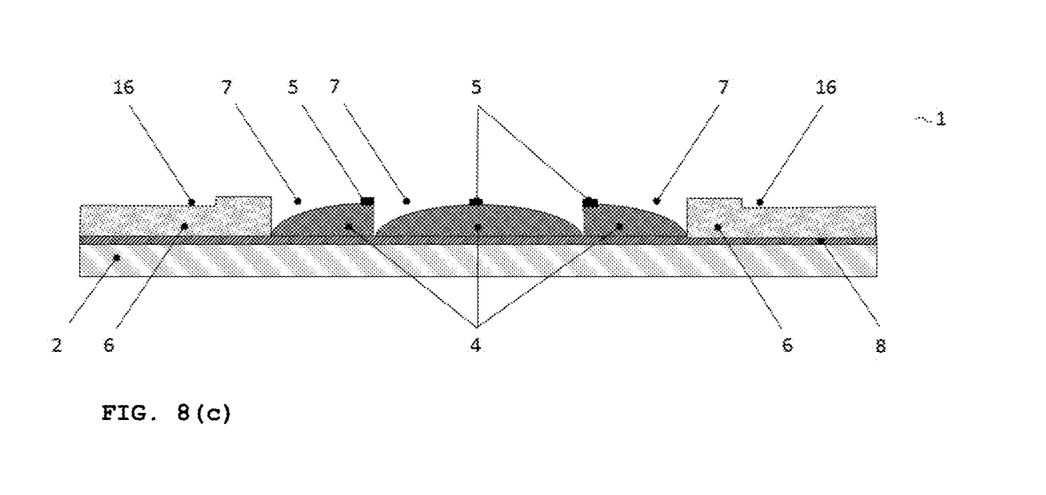

On the first optical transparent electrode (8), the border (6), the diffractive optical element (4) and a spacer (5) is formed. As illustrated by FIG. 8(b) a layer (18) of a material composition (12) is formed on the first optical transparent electrode (8). Using nanoimprint technology, the border (6), the diffractive optical element (4) and a spacer (5) are formed in this layer (18) as shown in FIG. 8(c), thereby creating a cavity (7) at the location of the diffractive optical element (4). This layer (18) can be a single layer or a stack of layers, whereby each layer can have a different material composition.

An alignment layer (11) is formed at the bottom of the cavity (7) to control the orientation of the liquid crystalline material (10) when present in the cavity (7). This alignment layer (11) can be created by forming submicron grooves in the surface of the diffractive optical structure (4) during the nanoimprint process. FIG. 3 illustrates a circular and a rectangular pattern of grooves in the top surface of the diffractive optical structure (4).

Figure 8D:
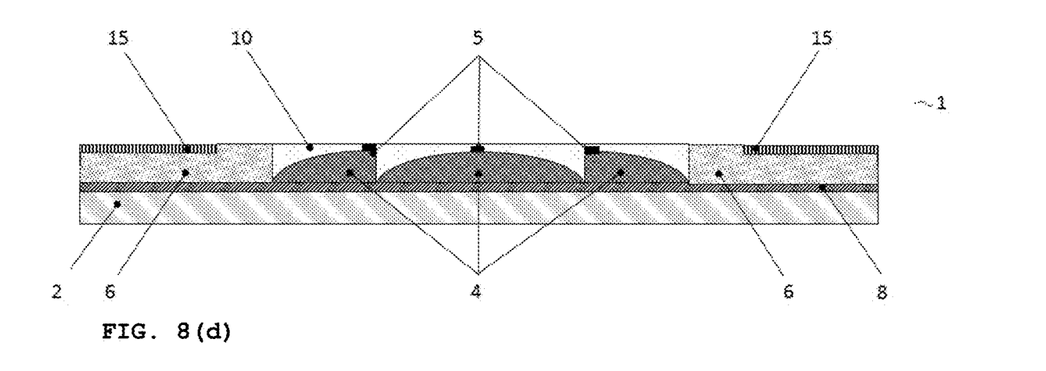
Figure 8E:
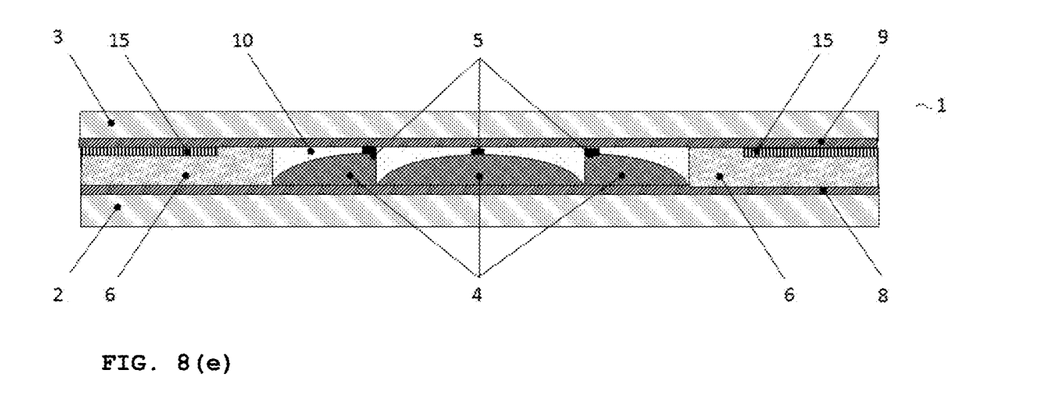

The cavity (7) may be filled and completed by a One Drop Fill process which starts by dispensing liquid crystalline material (10) in a micro-dispensed volume matching the volume of the cavity (7). Subsequently, the adhesive (15) is dispensed in the notch (16) present in the border (6) by using a dispensing or screen printing process as illustrated by FIG. 8(d). Typically the adhesive (15) can be a transparent UV-glue, a transparent thermal glue or a combination of both. The border minimizes cross-contamination between the adhesive part, i.e. the notch, and the electro-active part, i.e. the cavity (7), while creating a clear line between both parts.

Whereas the above steps describes the formation of the bottom part or substrate of the optical device (1), the upper part or substrate of the optical device (1) is formed by forming the second optical transparent thermoplastic layer (3) on another temporary carrier (not shown). The second optical transparent thermoplastic film (3) can be formed on this carrier by lamination. Typically the laminate film (3) is between 5 um and 1000 um thick. Alternatively, one may deposit a thermoplastic material in liquid form onto the carrier. The liquid material can then be either UV or thermally cured, thereby forming the first optical transparent thermoplastic film (3). Either way, a temporary adhesive may be needed to attach the second optical transparent thermoplastic film (3) to the carrier, allowing releasing the optical device (1) from the temporary carrier after completing of the processing. Temporary carrier solutions are available from companies such as TOK, BrewerScience, 3M, Nino, etc. In some cases the film (2) is fixated by applying a vacuum in between the film and the carrier.

On the second optical transparent thermoplastic layer (3), a transparent conductive film is formed to manufacture the second optical transparent electrode (9). This conductive film can be ITO. Because of the brittleness of ITO, less rigid and more flexible materials can be used such as PEDOT: PSS, graphene, carbon nanotubes or silver nanowires. On this second optical transparent electrode (9) another alignment layer (11) is formed to control the orientation of the liquid crystalline material (10) when present in the cavity (7).

To complete the One Drop Fill process as described above, this upper substrate is laminated on the bottom substrate using a vacuum lamination step as illustrated by FIG. 8(d). The glue layer (15) is cured through e.g. an UV step and/or a thermal step. This way ensures a fully closed cavity (7) is obtained with no interruption in the seal.

After laminating both substrates, the temporary carriers can be removed by debonding. The thus formed array of optical devices (1) is diced into individual planar optical devices (1) as shown in FIG. 1. This planar optical device (1) can then be curved by thermoforming as discussed above.

An alternative method for filling the cavity (7) with the liquid crystalline material (10) is to create during nanoimprint a channel (19) at least in the upper part of the border (6). FIG. 9 illustrates an optical device (1) having a channel (19) not only in the upper part but extending over the full height h of the border. The liquid crystalline material (10) is provided after the cavity (7) is closed by applying the second optical transparent thermoplastic layer (3). The closed cavity (7) of the individual optical devices (1) can then be filed with the liquid crystalline material (10).

Furthermore, the array of the optical devices (1) can also be thermoformed simultaneously by any of the above mentioned techniques with an appropriate mold. After thermoforming, the array is diced yielding the individual optical devices (1, 1').

While some embodiments have been illustrated and described in detail in the appended drawings and the foregoing description, such illustration and description are to be considered illustrative and not restrictive. Other variations to the disclosed embodiments can be understood and effected in practicing the claims, from a study of the drawings, the disclosure, and the appended claims. The mere fact that certain measures or features are recited in mutually different dependent claims does not indicate that a combination of these measures or features cannot be used. Any reference signs in the claims should not be construed as limiting the scope.

What is claimed is:

1. An optical device, comprising:
    a first optical transparent thermoplastic layer;
    a second optical transparent thermoplastic layer; and
    a border extending in between both thermoplastic layers thereby forming a sealed cavity and defining a refocusable optical zone, the sealed cavity containing:
        a diffractive optical element adjacent to the first optical transparent thermoplastic layer, wherein the diffractive optical element is a Fresnel lens having a plurality of lens structures mutually separated by grooves; and
        a plurality of physically separate spacers disposed in between a surface of the diffractive optical element facing the second optical transparent thermoplastic layer and the second optical transparent thermoplastic layer, wherein each spacer of the plurality of physically separate spacers is disposed on one of the plurality of lens structures.

2. The device of claim 1, wherein:
    the diffractive optical element, the spacer, and the border have the same material composition.

3. The device of claim 2, wherein:
    both the first optical transparent thermoplastic layer and the second optical transparent thermoplastic layer are curved.

4. The device of claim 1, wherein:
    the border comprises, remote from the cavity, a notch containing an adhesive in contact with the second optical transparent thermoplastic layer.

5. The device of claim 1, further comprising:
    a layer of a planarizing material covering the diffractive optical element, whereby at least part of the border adjacent to the diffractive optical element is made of the planarizing material; and
    the plurality of spacers, the planarizing layer, and the diffractive optical element being stacked on each other thereby maintaining a controlled distance between both thermoplastic layers.

6. The device of claim 1, further comprising:
    a first optical transparent electrode adjacent to the first optical transparent thermoplastic layer; and
    a second optical transparent electrode adjacent to the second optical transparent thermoplastic layer,
    whereby at least the sealed cavity is in between the first optical transparent electrode and the second optical transparent electrode.

7. An optical instrument comprising:
    at least one optical device, wherein the at least one optical device comprises:
    a first optical transparent thermoplastic layer;
    a second optical transparent thermoplastic layer; and
        a border extending in between both thermoplastic layers thereby forming a sealed cavity and defining a refocusable optical zone, the sealed cavity containing:
        a diffractive optical element adjacent to the first optical transparent thermoplastic layer, wherein the diffractive optical element is a Fresnel lens having a plurality of lens structures mutually separated by grooves; and
        a plurality of physically separate spacers disposed in between a surface of the diffractive optical element facing the second optical transparent thermoplastic layer and the second optical transparent thermoplastic layer, wherein each spacer of the plurality of physically separate spacers is disposed on one of the plurality of lens structures.

8. A method of manufacturing an optical device, the method comprising:
    providing a first optical transparent thermoplastic layer;
    forming by nanoimprint on the first optical transparent thermoplastic layer, at least one of a plurality of physically separate spacers, an optical diffractive element, and a border which encloses the optical diffractive element and the spacer, wherein the diffractive optical element is a Fresnel lens having a plurality of lens structures mutually separated by grooves; and
    providing a second optical transparent thermoplastic layer thereby forming a sealed cavity and defining a refocusable optical zone, the sealed cavity containing the plurality of spacers and the optical diffractive element,
    whereby the plurality of spacers are disposed in between a top surface of the optical diffractive element and the second optical transparent thermoplastic layer, and wherein each spacer of the plurality of physically separate spacers is disposed on one of the plurality of lens structures.

9. The method of claim 8, wherein forming by nanoimprint the plurality of spacers, the optical diffractive element and the border enclosing the optical diffractive element comprises:

providing a layer of a material composition on the first optical transparent layer; and nanoimprinting in the layer the plurality of spacers, the optical diffractive element, and the border enclosing the optical diffractive element, whereby the plurality of spacers and the optical diffractive element are stacked on each other thereby maintaining a controlled distance between both thermoplastic layers.

10. The method of claim 8, further comprising:

thermoforming the optical device thereby giving the first optical transparent thermoplastic layer and the second optical transparent thermoplastic layer a predetermined curvature.

11. The method of any of the claim 8, wherein nanoimprinting further comprises:

forming, at least in the upper part of the border, a channel extending through the border into the cavity.

12. The method of claim 8, wherein forming by nanoimprint the plurality of spacers, the optical diffractive element, and the border enclosing the optical diffractive element further comprises:

forming in the border, remote from the cavity, a notch for containing an adhesive in contact with the second optical transparent thermoplastic layer; and further comprising:

providing, prior to providing a second optical transparent thermoplastic layer, an adhesive in the notch only.

13. The method of claim 8, further comprising, prior to providing a second optical transparent thermoplastic layer:

providing a layer of planarizing material thereby covering the diffractive optical element and at least part of the border adjacent to the diffractive optical element; and nanoimprinting in the planarizing layer the plurality of spacers and part of the border, whereby the plurality of spacers, the planarizing layer, and the diffractive element are stacked on each other thereby maintaining a controlled distance between both the first optical transparent thermoplastic layer and the second optical transparent thermoplastic layer.

14. The method of claim 13, wherein forming by nanoimprint the plurality of spacers, the optical diffractive element, and the border enclosing the optical diffractive element comprises:

forming in the planarizing layer, remote from the cavity, a notch for containing an adhesive in contact with the second optical transparent thermoplastic layer; and further comprising:

providing, prior to providing the second optical transparent thermoplastic layer, an adhesive in the notch only.

15. The method of claim 8 further comprising:

forming a first optical transparent electrode adjacent to the first optical transparent thermoplastic layer; and forming a second optical transparent electrode adjacent to the second optical transparent thermoplastic layer, whereby at least the cavity is in between the first optical transparent electrode and the second optical transparent electrode.

16. The device of claim 1, further comprising liquid crystalline material, wherein the sealed cavity further contains the liquid crystalline material, and wherein the liquid crystalline material surrounds the plurality of spacers within the sealed cavity.

17. The optical device of claim 16, wherein the index of refraction of the liquid crystalline material is matched with the index of refraction of the diffractive optical element, the plurality of spacers, and the border at least for one state of the liquid crystalline material.

18. The optical device of claim 1, wherein the Fresnel lens comprises a central lens portion on which a spacer of the plurality of spacers is disposed.

19. The optical device of claim 1, wherein the diffractive optical element comprises a varying height in a lateral direction parallel to the first transparent layer, the varying height having at least one tip portion, and at least one groove portion, wherein the plurality of spacers are disposed on one of the tip portions.

* * * * *